United States Patent [19]
Choi et al.

[11] Patent Number: 6,162,644
[45] Date of Patent: Dec. 19, 2000

[54] METHOD FOR CONTROLLING AND OPTIMIZING XYLENE ISOMER SEPARATION AND ISOMERIZATION PROCESS USING NEAR INFRARED ANALYZER SYSTEM AND APPARATUS FOR CARRYING OUT SAME

[75] Inventors: Sun Choi; Yong-Sueng Kim; Hoe-Il Chung; Suk-Joon Kim; Joon-Sik Lee; Min-Sik Ku; Young-Hwan Kim, all of Ulsan, Rep. of Korea

[73] Assignee: SK Corporation, Seoul, Rep. of Korea

[21] Appl. No.: 09/268,804

[22] Filed: Mar. 16, 1999

[30] Foreign Application Priority Data

Mar. 24, 1998 [KR] Rep. of Korea .................. 98-10123

[51] Int. Cl.[7] .................. G01N 35/08; G01N 21/00; G05D 7/00
[52] U.S. Cl. .................. 436/55; 422/62; 422/111
[58] Field of Search .................. 422/62, 67, 108, 422/111; 436/55

[56] References Cited

U.S. PATENT DOCUMENTS

| 4,111,218 | 9/1978 | Hobbs .................. 137/2 |
| 4,621,062 | 11/1986 | Stewart et al. .................. 436/55 |
| 5,470,482 | 11/1995 | Holt .................. 210/662 |
| 5,624,846 | 4/1997 | Hayashibe et al. .................. 436/50 |
| 5,879,629 | 3/1999 | Capuano et al. .................. 422/82 |

FOREIGN PATENT DOCUMENTS

94-15408 6/1994 Rep. of Korea .

*Primary Examiner*—Jill Warden
*Assistant Examiner*—Brian R. Gordon
*Attorney, Agent, or Firm*—Seidel, Gonda, Lavorgna & Monaco, PC

[57] ABSTRACT

A method for and an apparatus for controlling and optimizing a xylene isomer separation and isomerization process, in which near infrared light of a wavelength ranging from 1,100 nm to 2,500 nm is transmitted through samples obtained at different stages of the process from raw materials flowing in the process by use of an analyzer system using optical fibers, thereby simultaneously measuring, in an on-line manner, xylene isomers and aromatic hydrocarbons containing 6 to 9 carbon atoms from those samples. Accordingly, it is possible to monitor the entire operation state of the process within 15 minutes in an on-line manner. Conventionally, 2 to 3 days are taken for the same monitoring.

9 Claims, 5 Drawing Sheets

METHOD FOR CONTROLLING AND OPTIMIZING XYLENE ISOMER SEPARATION AND ISOMERIZATION PROCESS USING NEAR INFRARED ANALYZER SYSTEM AND APPARATUS FOR CARRYING OUT SAME

BACKGROUND OF THE INVENTION

1. Field of the Invention

The present invention relates to a method for controlling and optimizing a xylene isomer separation and isomerization process using a near infrared analyzer system, and more particularly to a method and an apparatus for controlling and optimizing a xylene isomer separation and isomerization process, in which near infrared light of a wavelength ranging from 1,100 nm to 2,500 nm is transmitted through samples obtained at different stages of the process from raw materials flowing in the process by use of an analyzer system using optical fibers, thereby simultaneously measuring, in an on-line manner, xylene isomers and aromatic hydrocarbons containing 6 to 9 carbon atoms from those samples.

2. Description of the Prior Art

Figure 1:
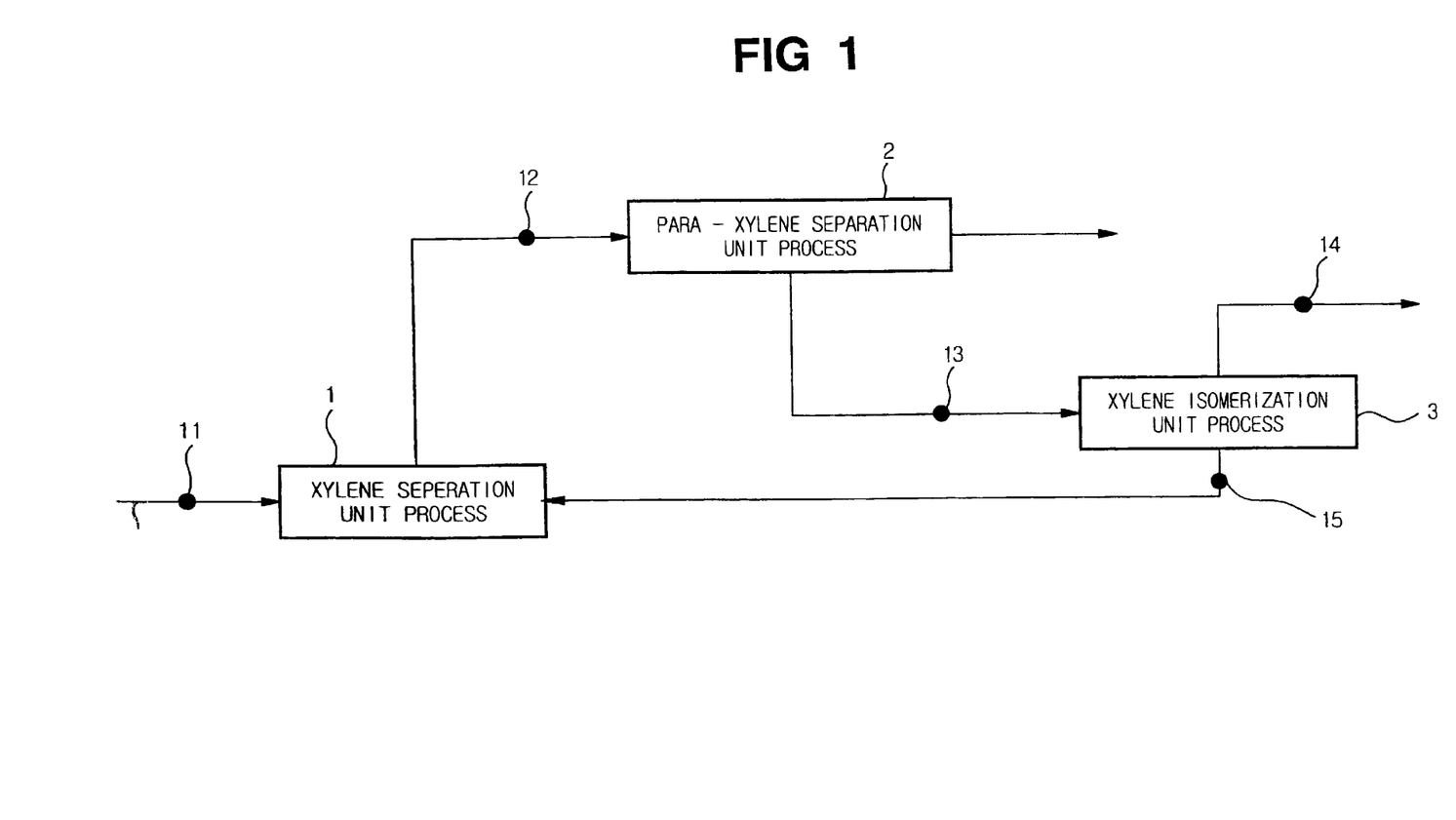
FIG. 1 is a block diagram illustrating measuring points in a general xylene isomer separation and isomerization process selected in accordance with the present invention.

Referring to FIG. 1, a typical xylene isomer separation and isomerization process is illustrated. As shown in FIG. 1, such a xylene isomer separation and isomerization process mainly involves a xylene separation unit process, para-xylene separation unit process, and a xylene isomerization unit process, which processes are denoted by the reference numerals 1, 2, and 3, respectively, in FIG. 1. The raw material, which is processed in the xylene separation unit process, contains a large part of xylene isomer, ethylbenzene, toluene, and aromatic components. The xylene isomer is a mixture of meta-xylene, ortho-xylene, and para-xylene. In the xylene separation unit process, C9 aromatic components and ortho-xylene (partially) are separated from the raw material. The resultant material is then sent to the para-xylene separation unit process. In this para-xylene separation unit process, para-xylene is separated from the material. Thus, production of para-xylene is achieved. The resultant material containing xylene isomers other than para-xylene is then sent to the xylene isomerization unit process. Reactions carried out in the xylene isomerization unit process include an isomerization, in which the xylene isomers other than para-xylene are converted to have an equilibrium concentration, and a dealkylation, in which ethylbenzene is converted into benzene. The resultant material is then separated into a benzene product and an xylene isomer. The separated xylene isomer is subsequently circulated to the xylene separation unit process.

Meanwhile, in such a xylene isomer separation and isomerization process, several on-line and off-line gas chromatography devices have been used for analysis of process operations and process performances. Gas chromatography requires lengthened analysis time from 15 minutes to about one hour and a requirement for the use of a plurality of gas chromatography devices corresponding to respective stages where a required measurement is to be carried out. For these reasons, on-line gas chromatography devices have been used only to continuously check a few essential components associated with an optimum process operation, thereby obtaining products with a good quality.

In order to achieve a more accurate control and an optimization for processes, it is essentially required to calculate process performances of all unit processes used and the entire process. For such a process performance calculation, it is also required to analyze all components of respective materials to be processed in unit processes and respective product streams emerging from those unit processes. Typically, such a component analysis is carried out by obtaining samples in the production field, and measuring required components from those samples in the laboratory using an off-line gas chromatography device. However, such procedures require a lot of time. For this reason, in the case of the above mentioned xylene isomer separation and isomerization process, the process performance analysis is carried out only one time in a week. Based on the analysis results, process parameters are controlled. The process performance of the xylene isomer separation and isomerization process varies frequently depending on various variations occurring at the upstream stage from each unit process where a raw material to be processed is supplied. However, conventional process performance monitoring and process parameter control, which are carried out based on a component analysis using on-line and off-line gas chromatography devices, can not effectively cope with such variations.

On the other hand, U.S. Pat. No. 5,470,482 discloses a process control method in which control of fluidizing beds is carried out based on the purity or degree of recovery of para-xylene. In accordance with this method, the contents of para-xylene, ortho-xylene, meta-xylene, and ethylbenzene in pumparound and pusharound streams in a fluidizing beds are measured. Based on the measurement results, the purity or degree of recovery of para-xylene is calculated. The entire process is controlled in accordance with the relationships of the calculated purity or degree of recovery of para-xylene with operation parameters. This method is characterized in that control of fluidizing beds can be rapidly and efficiently achieved by measuring information required for separation control using an infrared and near infrared spectroscopy. However, this patent only shows the concept of measurement without any concrete implementing examples.

Meanwhile, Korean Patent Application No. 94-15408 discloses a process control method in which control of xylene-free fluidizing beds is carried out using a Raman spectroscopy. In accordance with this method, the chemical composition of a mixture of aromatic hydrocarbon isomers containing 8 to 10 carbon atoms is measured using a Raman spectrum. Based on the measurement result, the concentration profile of isomers in the mixture is reconstructed. The reconstructed concentration profile is then compared with a reference concentration profile determined by one or more operation parameters of a processing and controlling means used in the separation process. This method is characterized in that a distillation or crystallization process for obtaining para-xylene or ortho-xylene is carried out by controlling a simulated fluidizing bed. This method is basically different from the above mentioned method using near infrared because it uses a Raman spectroscopy to control xylene-free fluidizing beds.

After repeated experiments, the inventors could find that when particular stages in the xylene isomer separation and isomerization process are measured using a near infrared analyzer system, it is possible to solve the difficulties in process performance monitoring and process parameter control encountered upon using the above mentioned conventional component analysis based on a gas chromatography.

SUMMARY OF THE INVENTION

Therefore, an object of the invention is to provide a method and an apparatus for controlling and optimizing a xylene isomer separation and isomerization process, in which information required for separation control for samples is measured using a near infrared analyzer system, thereby effectively controlling and optimizing the xylene isomer separation and isomerization.

In accordance with one aspect, the present invention provides a method for controlling and optimizing a xylene isomer separation and isomerization process using a near infrared analyzer system, comprising the steps of: (A) extracting samples at the upstream stage from a xylene separation unit process, the upstream stage from a para-xylene separation unit process, the upstream stage from a xylene isomerization process, the upper-side downstream stage of a C7 separation process, and the lower-side downstream stage of the C7 separation process, respectively; (B) collecting the extracted samples in a fast loop via each feed lines; (C) carrying out a primary heat exchange in a primary heat exchange system for the samples fed from the fast loop by cooling water supplied from a cooling water line; (D) determining whether or not respective temperatures of the samples heat-exchanged in the primary heat exchange system are not more than a first predetermined temperature; (E) secondarily cooling the samples, which have been cooled to the first predetermined temperature or less, by a chiller included in a secondary cooling system; (F) determining whether or not respective temperatures of the samples cooled in the secondary cooling system are not more than a second predetermined temperature; (G) sequentially selecting the samples cooled to the second predetermined temperature or less by a stream selector, and determining which sample has been selected from the first to the fifth samples; (H) partially extracting the sequentially selected samples by desired amounts, respectively, while returning the remaining portions of the samples to step (A) via first return lines, the fast loop, and second return lines; (I) sequentially detecting the components of the samples each extracted by a desired amount, by use of a probe, and then sequentially returning the samples to a sample recovery line via a third feed return line; (J) sequentially analyzing the samples, detected by the probe, in a near infrared analyzer, in accordance with a near infrared spectroscopy, in terms of ethylbenzene conversion, benzene selectivity, xylene loss, catalyst activity, para-xylene equilibrium constant, ortho-xylene equilibrium constant, para-xylene yield, and ortho-xylene yield; (K) sending data, obtained after the analysis for the samples in the near infrared analyzer, to a distributed control system in an on-line manner; (L) sending data resulting from a processing for the analysis data in the distributed control system to a process computer; (M) outputting the data received in the process computer in the form of a signal easily recognizable by an operator; (N) recognizing the data, which is displayed by the process computer, by the operator, inputting a desired command value by the operator, based on his determination made after his recognition, to the distributed control system; and (O) determining the input command value, thereby controlling valves for the samples to be opened or closed.

In accordance with another aspect, the present invention provides an apparatus for controlling and optimizing a xylene isomer separation and isomerization process using a near infrared analyzer system, comprising: feed lines for extracting samples at a xylene feed stage, the upstream stage from a para-xylene separation unit process, the upstream stage from a xylene isomerization process, the upper-side downstream stage from a C7 separation process, and the lower-side downstream stage from the C7 separation process; a fast loop for accelerating the samples fed thereto via the feed lines to a predetermined flow rate or more; a primary heat exchange system for performing heat exchange with the samples fed thereto in an accelerated state, thereby cooling the samples to a first predetermined temperature; a secondary cooling system for secondarily cooling the samples, primarily cooled in the primary heat exchange system, to a second predetermined temperature; a cooling water line for supplying cooling water to the primary heat exchange system; a chiller for cooling water introduced from the cooling water line to a desired temperature and then supplying the cooled water to the secondary cooling system; a stream selector for sequentially selecting and discharging the samples cooled to a desired temperature in the secondary cooling system; a probe for detecting the components of a sample selectively fed thereto in a desired quantity; first return lines for returning the remaining portions of the samples, except for the sample portions fed to the probe for the component detection, to the fast loop, in an accelerated state; second return lines for returning the samples, returned via the first return lines and accelerated again by the fast loop, to the upstream stage from the xylene separation unit process, the upstream stage from the para-xylene separation unit process, the upstream stage from the xylene isomerization process, the upper-side downstream stage of the C7 separation process, and the lower-side downstream stage of the C7 separation process, respectively; a second return line for returning the sample from the probe to a sample recovery line after the component detection for the sample by the probe is completed; a near infrared analyzer for analyzing component data detected by the probe and outputting the analyzed result in the form of an electrical signal in an on-line manner; a distributed control system for performing a distributed control for data received from the near infrared analyzer, sending the resultant signal to a process computer, determining a command value inputted by an operator on the basis of the result of his comparison for the data displayed through the process computer with set data, and performing a control for opening and closing a valve associated with the data; and the process computer for displaying the data received from the distributed control system in such a fashion that the operator can easily recognize the displayed data, and outputting the data.

BRIEF DESCRIPTION OF THE DRAWINGS

Other objects and aspects of the invention will become apparent from the following description of embodiments with reference to the accompanying drawings in which.

DESCRIPTION OF THE PREFERRED EMBODIMENTS

Figure 2:
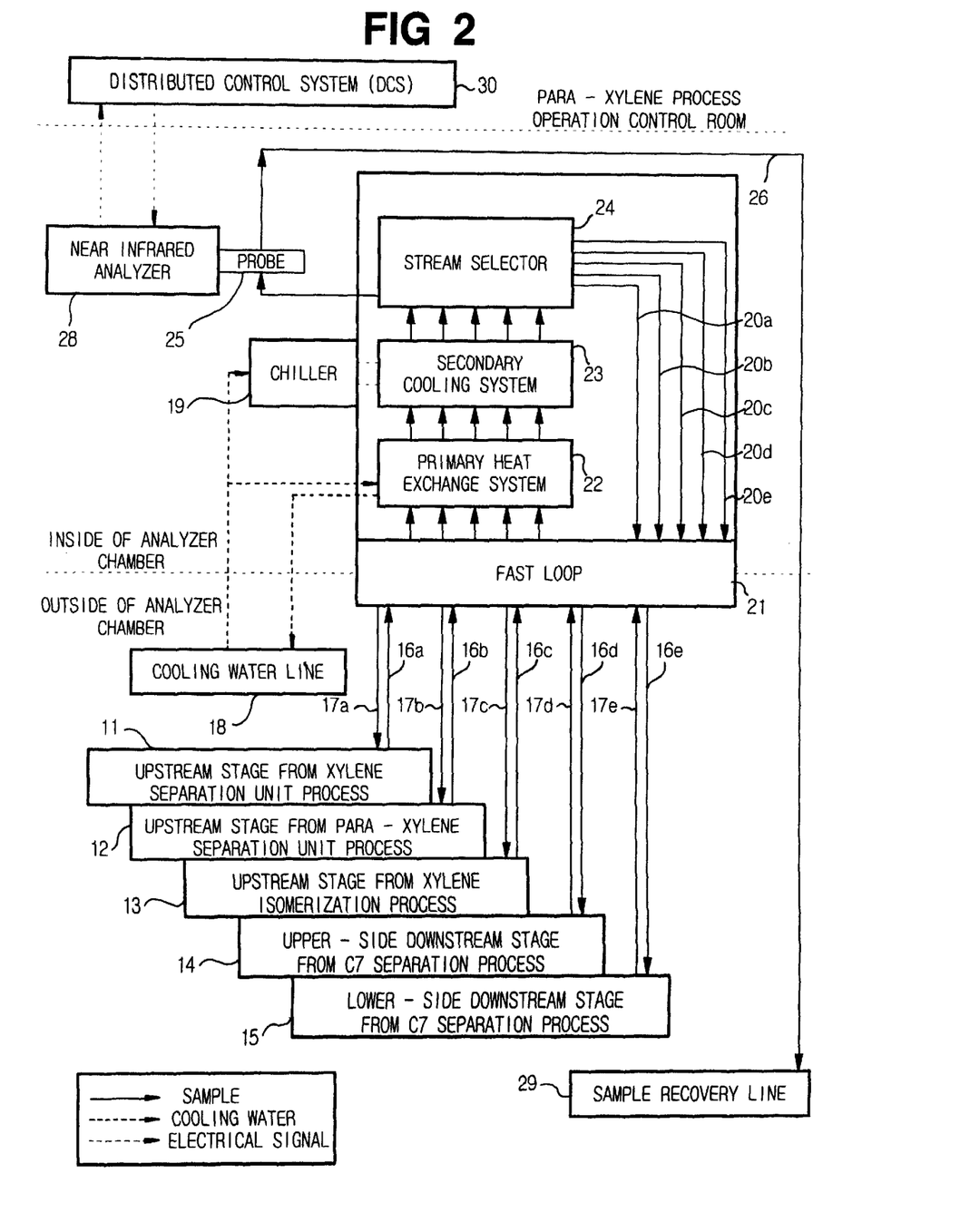
FIG. 2 is a block diagram illustrating an apparatus for controlling and optimizing a xylene isomer separation and isomerization process in accordance with the present invention, in which a distributed control system using a near infrared analyzer system is provided.

The present invention is concerned with a method for controlling and optimizing a xylene isomer separation and isomerization process, in which near infrared light of a wavelength ranging from 1,100 nm to 2,500 nm is transmitted through samples obtained at different stages of the process from raw materials flowing in the process by use of an analyzer system using optical fibers, thereby simultaneously measuring, in an on-line manner, xylene isomers and aromatic hydrocarbons containing 6 to 9 carbon atoms from those samples. The analyzer system is designed to simultaneously measure, by use of a single near infrared spectrometer, five stages of the xylene isomer separation and isomerization process, for example, the xylene feed stage 11, the upstream stage 12 from the para-xylene separation unit process, the upstream stage 13 from the xylene isomerization process, namely, C7 separation process, the upper-side downstream stage 14 from the C7 separation process, and the lower-side downstream stage 15 from the C7 separation process, as shown in FIG. 2.

The reason why the above mentioned five stages are simultaneously measured is to monitor the state of the entire process. If the measurement is omitted even at one of the above mentioned stages, it is then difficult to monitor the state of the entire process.

In accordance with the method of the present invention, it is possible to analyze chemical compositions at all the five stages within 15 minutes. Accordingly, chemical composition information required for the operation of the entire process and desired process efficiency can be rapidly obtained.

For the near infrared spectrometer in the present invention, well-known near infrared spectrometers may be optionally used. Now, the measurement principle of the near infrared spectrometer will be briefly described. Overtone and combination absorption bands of hydrocarbons appear in the near infrared range. Each hydrocarbon has an intrinsic absorption band. In the case of a hydrocarbon mixture, absorption bands of hydrocarbons thereof overlap with one another. For this reason, it is impossible to achieve a separation of components and a measurement of compositions of those components. In such a case, accordingly, the composition of those component is analyzed using a multivariate regression method which is a statistical calibration method. In particular, xylene isomers including ortho-xylene, meta-xylene, and para-xylene exhibit near infrared spectrums which are very similar in qualitative characteristics. However, where the pathlength of near infrared measurement and analyzing wavelength are optimized, the contents of xylene isomers (ortho-xylene, meta-xylene, and para-xylene), ethylbenzene, non-aromatic hydrocarbon, toluene, benzene, and aromatic components having more than 9 carbons can be simultaneously measured without physical separation thereof. The compositions of those components at the above mentioned five important stages of the xylene isomer separation and isomerization process are analyzed in substantially real time. Accordingly, it is possible to rapidly monitor the operation state of the entire process.

Figure 3:
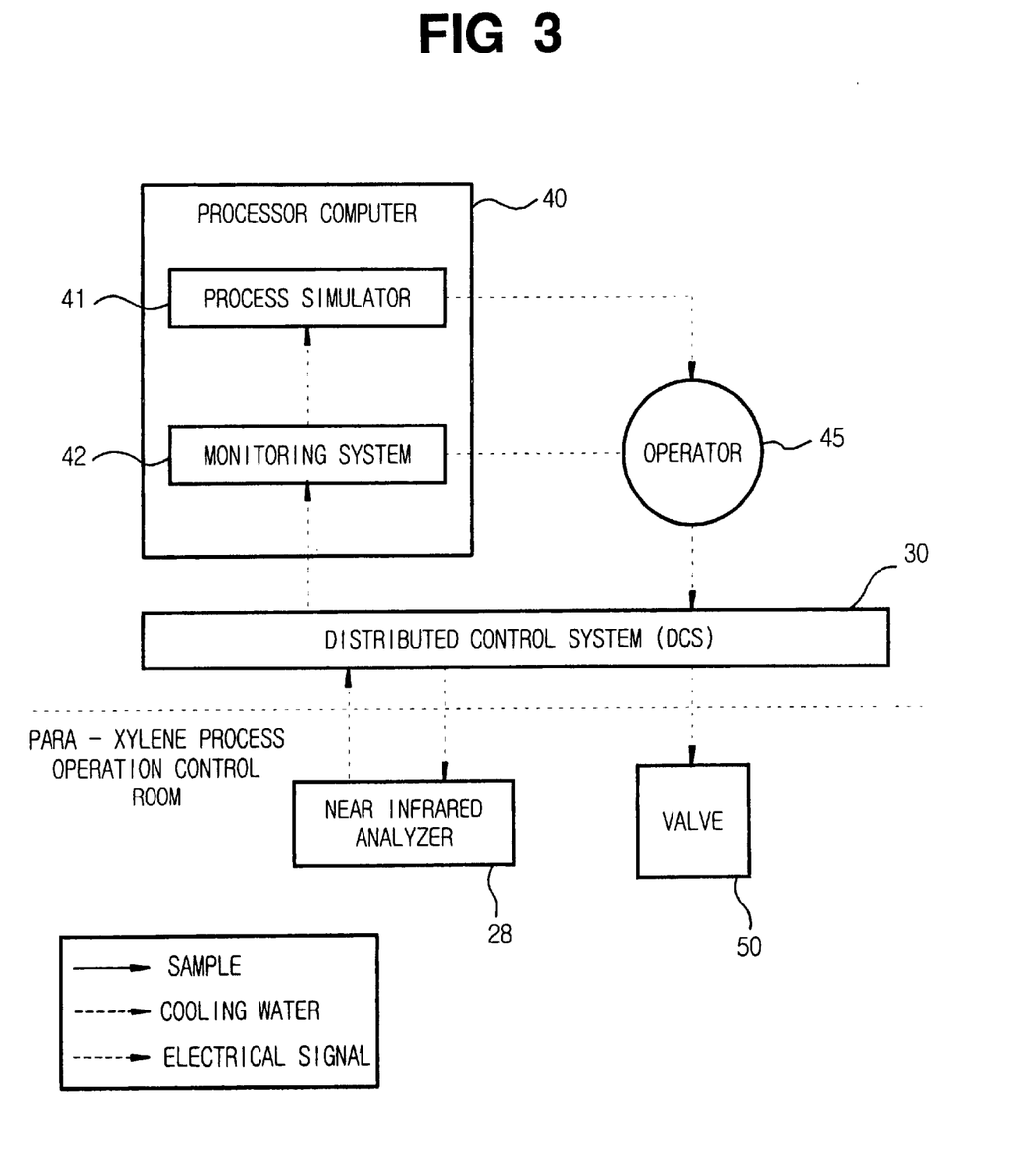
FIG. 3 is a block diagram illustrating the relation among the near infrared analyzer system, distributed control system and monitoring system included in the apparatus of FIG. 2.

FIG. 2 illustrates the entire configuration of an apparatus for carrying out the method for controlling and optimizing a xylene isomer separation and isomerization process in accordance with the present invention, in which a distributed control system using a near infrared analyzer system is provided. FIG. 3 is a block diagram illustrating the relation among the near infrared analyzer system, distributed control system and monitoring system.

Referring to FIG. 2, feed lines 16a to 16e are shown which extract samples at five stages of the xylene isomer separation and isomerization process and feed those samples to a fast loop 21. The stages, where samples are obtained, may be a xylene feed stage 11 in the xylene feed line 4, namely, the upstream stage 11 from the xylene separation unit process, the upstream stage 12 from the para-xylene separation unit process, the upstream stage 13 from the xylene isomerization process, namely, C7 separation process, the upper-side downstream stage 14 from the C7 separation process, and the lower-side downstream stage 15 from the C7 separation process, as shown in FIG. 1.

The fast loop 21 serves to accelerate the samples fed thereto via the feed lines 16a to 16e to a predetermined flow rate or more. Preferably, the fast loop 21 is configured to completely feed the samples to a near infrared analyzer 28 within about 30 seconds using a differential pressure in the process ranging from about 7 Kg/cm$^2$ to 20 Kg/cm$^2$.

A primary heat exchange system 22 is connected to the fast loop 21. This primary heat exchange system 22 serves to perform heat exchange with the samples, thereby cooling those samples to a desired temperature of, for example, about 45° C. Cooling water circulates in the primary heat exchange system to cool the hot samples.

A secondary cooling system 23 is arranged downstream from the primary heat exchange system 22. The secondary cooling system 23 secondarily cools the samples, primarily cooled in the primary heat exchange system 22, to a desired temperature of, for example, about 25° C. This secondary cooling system 23 includes a chiller 19 so that it cools, in a controlled manner, the samples to a temperature desired for a near infrared measurement sensitive to temperature. The chiller 19 cools the cooling water introduced from a cooling water line 18 to a desired temperature and then supplies the cooled water to the secondary cooling system 23.

The cooling water line 18 supplies the cooling water to the primary heat exchange system 22. A stream selector 24, which is arranged downstream from the secondary cooling system 23, sequentially selects the samples cooled to a desired temperature in the secondary cooling system 23 so that the samples are fed to be sequentially measured. The stream selector 24 carries out selection of a sample stream desired to be measured, using pneumatic pressure. That is, the stream selector 24 controls a desired electronic valve thereof based on a pneumatic pressure generated in accordance with a control signal from a process computer 40 (FIG. 3). The stream selector 24 feeds a selected sample to a probe 25 in a flow rate of, for example, about 300 cc per minute. The stream selector 24 is provided with a plurality of solenoid valves in order to sequentially send respective portions of the samples introduced therein to the probe 25 while also sending the remaining portions of those samples to first return lines 20a to 20e, respectively.

The probe 25 serves to detect the components of a sample selectively fed thereto in a desired quantity. In the probe 25, a near infrared radiation, which is emitted through an optical fiber, is transmitted through the sample and then sent to a spectrometer via the optical fiber. In the spectrometer, the near infrared spectrum of the light is measured.

The first return lines 20a to 20e return the remaining portions of the samples, except for the sample portions fed to the probe 25 for a component detection, to the fast loop 21 so as to return those remaining sample portions to associated original stages in an accelerated state. For such sample return, second return lines 17a to 17e are also connected between the fast loop 21 and respective stages where samples are extracted. That is, the second return lines 17a to 17e return the samples, returned via the first return lines 20a to 20e and accelerated by the fast loop 21, to the upstream stage 11 from the xylene separation unit process, the upstream stage 12 from the para-xylene separation unit process, the upstream stage 13 from the xylene isomerization process, namely, C7 separation process, the upper-side downstream stage 14 of the C7 separation process, and the lower-side downstream stage 15 of the C7 separation process, respectively.

A third return line 26 is also connected to the probe 25 in order to return the sample from the probe 25 to a sample recovery line 29 after a component detection for the sample by the probe 25 is completed. The return of the sample through the third return line 26 is automatically carried out by virtue of a differential pressure of the sample. Accordingly, it is unnecessary to use any separate drive motor or feeding device.

Thus, the first return lines 17a to 17e, the second return lines 20a to 20e, and the third return line 26 can automatically recover the samples by virtue of a pressure difference between the stream selector 24 and fast loop 21, a pressure difference between the fast loop 21 and each unit process, and a pressure difference between the probe 25 and the sample recovery line 29. Each of the feed lines 16a to 16e and return lines 17a to 17e, 20a to 20e, and 26, may have a minimum diameter in so far as it can feed a liquid therethrough.

The near infrared analyzer 28 analyzes component data detected by the probe 25 and outputs the analyzed result in the form of an electrical signal in an on-line manner.

A distributed control system 30 is coupled to the near infrared analyzer 28. The distributed control system 30 performs a distributed control for data received from the near infrared analyzer 28 and sends the resultant signal to the process computer 40 which, in turn, displays sample data corresponding to the received signal. After monitoring the displayed sample data, the operator, who is denoted by the reference numeral 45 in FIG. 3, compares the displayed data with set data. When the operator 45 inputs a desired command value to the process computer 40, based on the result of the comparison, the process computer 40 performs a control for opening or closing a desired valve denoted by the reference numeral 50 in FIG. 3.

The process computer 40 is configured to display the data received from the distributed control system 30 in such a fashion that the operator 45 can easily recognize the displayed data. As shown in FIG. 3, the process computer 40 includes a monitoring system 42 provided with a display means for displaying data in such a fashion that the operator can easily recognize the displayed data with the naked eye. The process computer 40 also includes a process simulator 41 for carrying out a process simulation for determining optimum process operation parameters, based on the measured results obtained from the near infrared analyzer system and the process performance evaluation parameters supplied from the monitoring system 42. The process simulator 41 also has a function for copying or transmitting the data displayed on the monitoring system 42.

Alternatively, it is possible to use a configuration in which the valve 50 is automatically opened and closed, based on data set in the distributed control system 30 without being controlled by a manual operation of the operator 45 based on his determination on the basis of the data displayed on the monitoring system 42 of the process computer 40.

The near infrared analyzer 28 includes an infrared light emitting lamp, a monochromator, a detector, an optical fiber, an automatic sample pre-processing unit, and an automatic sample feeding unit. A tungsten-halogen lamp may be used for the near infrared light emitting lamp. A holographic grating may be used for the monochromator. The detector may comprise a PbS (lead sulfide) detector. The automatic sample feeding unit is designed to feed a sample from the process to the near infrared analyzer (or spectrometer) via the fast loop 21 within one minute. On the other hand, the automatic sample pre-processing unit is designed to cool a hot sample to a temperature of 25° C. while filtering foreign matters from the sample.

The near infrared spectrum obtained by the near infrared analyzer 28 is converted into a second derivative spectrum. Based on the second derivative spectrum, the chemical composition of the associated sample is measured using a partial least squares method. Such a second derivative spectrum is a spectrum obtained by secondarily differentiating a near infrared spectrum. The second derivative spectrum is free of a variation in the base line thereof caused by a variation in the intensity of the emitted light and a variation in the alignment of the spectrometer. The partial least squares method is a method in which the axes of the near infrared spectrum are rearranged in such a manner that maximum variations in measured components are exhibited, and a calibration equation is made through a regression analysis for the resultant near infrared spectrum. This partial least squares method can be effectively used for analysis for a complex mixture.

Meanwhile, the analysis results obtained in accordance with the present invention are used for on-line monitoring, process control and process optimization for the para-xylene process, as shown in FIG. 3. The near infrared analyzer system periodically analyzes compositions of material streams at five desired stages in the above mentioned process at a time interval of 15 minutes in an on-line manner. The analyzed results are sent to the monitoring system 42 included in the process computer 40 via the distributed control system.

Figure 4A:
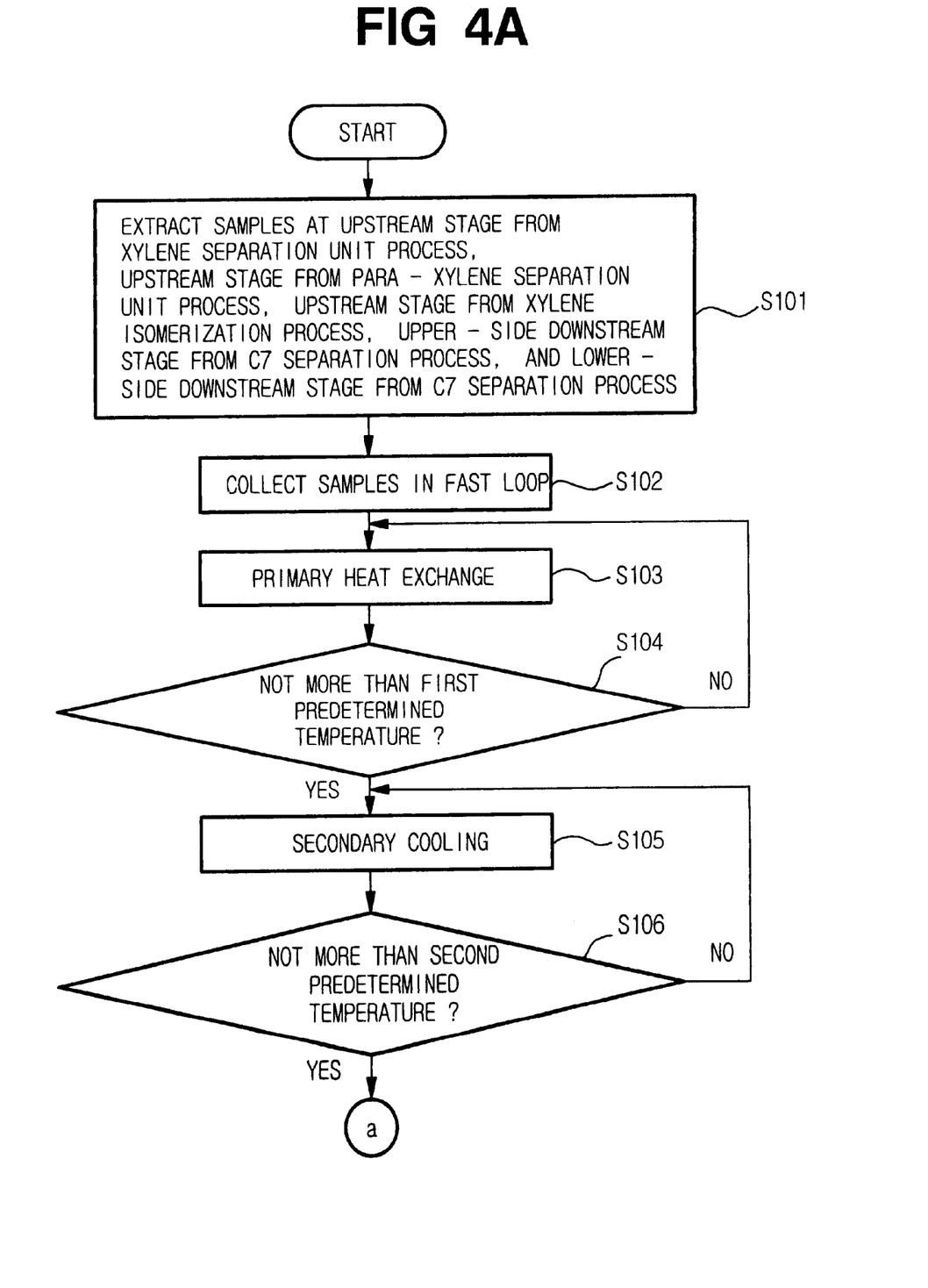
FIGS. 4A and 4B comprise a flow chart illustrating a method for controlling and optimizing a xylene isomer separation and isomerization process by use of the apparatus of FIG. 2 in accordance with the present invention.
Figure 4B:
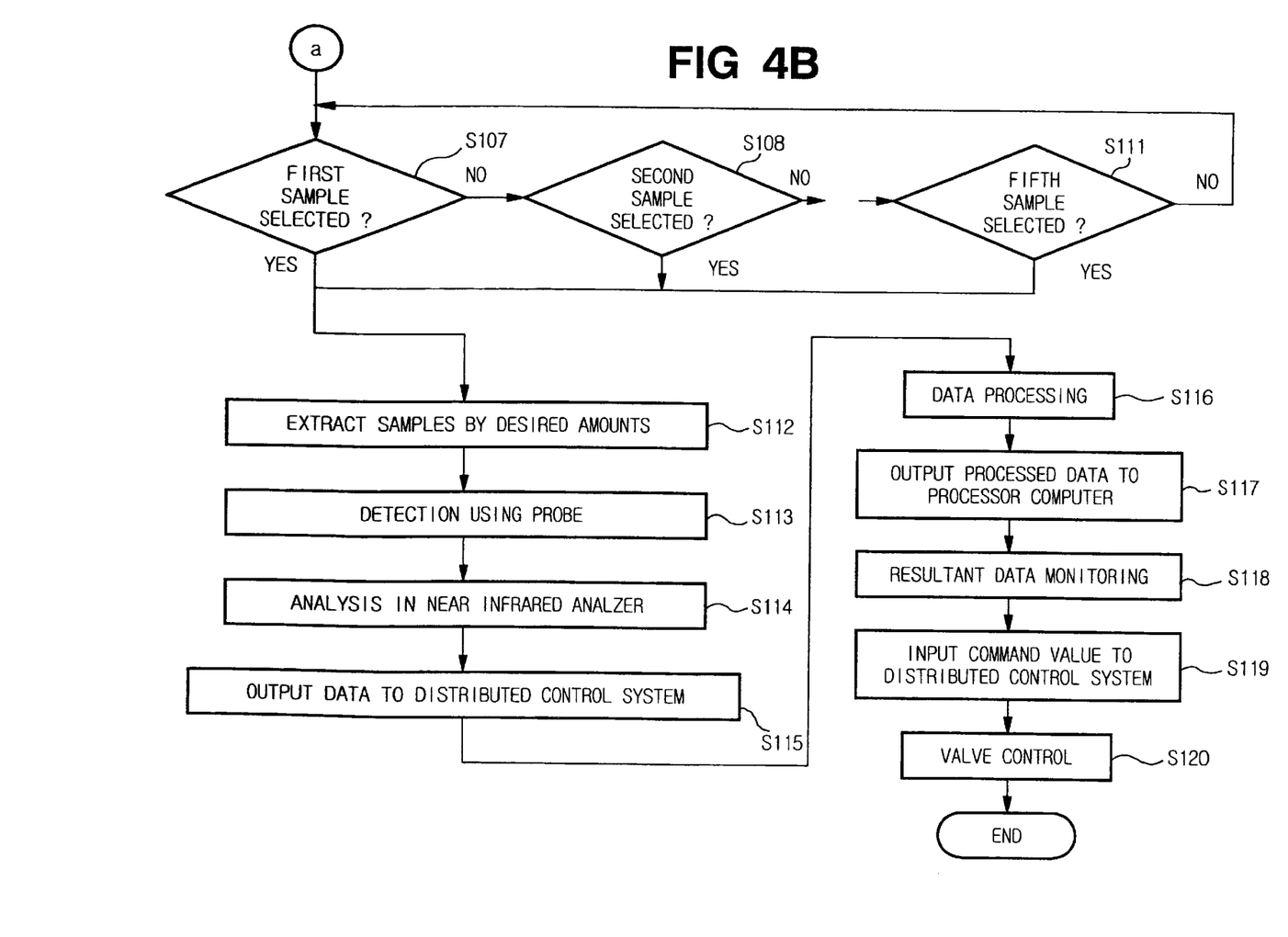

Now, the method for controlling and optimizing a xylene isomer separation and isomerization process using the above mentioned apparatus in accordance with the present invention will be described in conjunction with a flow chart shown in FIGS. 4A and 4B.

In accordance with this method, at step S101, samples are extracted at the upstream stage 11 from the xylene separation unit process, the upstream stage 12 from the para-xylene separation unit process, the upstream stage 13 from the xylene isomerization process, namely, C7 separation process, the upper-side downstream stage 14 of the C7 separation process, and the lower-side downstream stage 15 of the C7 separation process, respectively. The extracted samples are collected in the fast loop 21 via the feed lines 16a to 16e, respectively, at step S102.

At step S103, a primary heat exchange is then carried out in the primary heat exchange system 22 for the samples fed from the fast loop 21 by cooling water supplied from the cooling water line 18. Subsequently, it is determined at step S104 whether or not respective temperatures of the samples heat-exchanged in the primary heat exchange system 22 are not more than a first predetermined temperature.

Thereafter, the samples, which have been cooled to the first predetermined temperature or less, are secondarily cooled by the chiller 27 included in the secondary cooling system 23, at step S105. It is then determined at step S106 whether or not respective temperatures of the samples cooled in the secondary cooling system 23 are not more than a second predetermined temperature.

Steps S107 to S111 are then sequentially executed. At these steps S107 to S111, the samples cooled to the second predetermined temperature or less are sequentially selected by the stream selector 24. It is then determined which sample has been selected from the first to the fifth samples. Thereafter, the sequentially selected samples are partially extracted by desired amounts, respectively, at step S112. The remaining portions of the samples are then returned to step S101 via the first return lines 20a to 20e, fast loop 21, and second return lines 17a to 17e. At this time, the return of the samples is automatically carried out by virtue of pressure differences among return lines. Accordingly, it is unnecessary to use any drive motor or feeding device. This enables a semi-permanent use of the system.

At step S113, the probe 25 then detects the components of each sample extracted by a desired amount. After the detection, the sample is returned to the sample recovery line 29 via the third feed return line 26.

Thereafter, the near infrared analyzer 28 analyzes, at step S114, each sample detected by the probe 25, in accordance with a near infrared spectroscopy, in terms of ethylbenzene conversion, benzene selectivity, xylene loss, catalyst activity, para-xylene equilibrium constant, ortho-xylene equilibrium constant, para-xylene yield, and ortho-xylene yield. At step S115, data obtained after the analysis for each sample in the near infrared analyzer 28 is then sent to the distributed control system 30 in an on-line manner.

Data resulting from a processing for the analysis data in the distributed control system 30 at step S116 is then sent to the process computer 40 at step S117. At step S118, the process computer 40 then outputs the received data in the form of a signal which can be easily recognized by the operator 45.

At step S119, the operator 45 then recognizes the data displayed by the process computer 40 and inputs a desired command value, based on his determination made after his recognition, to the distributed control system 30. This distributed control system 30 determines the input command value at step S120, thereby controlling the valve 50 for each sample. Thus, the valves 50 for all samples are automatically opened or closed.

The above mentioned near infrared analyzer system calculates the process yield of the entire process, based on the results of the analysis as well as the compositions of material streams at five stages in the process. The near infrared analyzer system also calculates important process performance evaluation parameters for the xylene isomerization process, namely, ethylbenzene conversion, benzene selectivity, xylene loss, catalyst activity, para-xylene equilibrium constant, ortho-xylene equilibrium constant, para-xylene yield, and ortho-xylene yield. The calculated results are displayed through the monitoring system.

As shown in FIG. 3, the xylene isomer separation and isomerization process includes a xylene separation unit process, a para-xylene separation unit process, and a xylene isomerization unit process. The xylene separation unit process uses one or more distillation columns. The raw material, which is processed in the xylene separation unit process, contains a large part of xylene isomer, ethylbenzene, toluene, and aromatic components with more than 9 carbon atoms. The xylene isomer is a mixture of meta-xylene, ortho-xylene, and para-xylene. In the xylene separation unit process, C9 aromatic components are separated from the raw material. The resultant material is then sent to the para-xylene separation unit process. An additional distillation column may be used in the xylene separation unit process in order to produce ortho-xylene. The para-xylene separation unit process uses one absorption column and two or more distillation columns. In the para-xylene separation unit process, para-xylene is separated from the material, using the absorption column. Thus, para-xylene is produced. The xylene isomerization unit process uses one reactor system and one or more distillation columns. The material emerging from the para-xylene separation unit process and containing xylene isomers other than para-xylene is then sent to the xylene isomerization unit process. Reactions carried out in the xylene isomerization unit process include an isomerization, in which the xylene isomers other than para-xylene are converted to have an equilibrium concentration, and a dealkylation, in which ethylbenzene is converted into benzene. The resultant material is then separated into a benzene product and a xylene isomer. The separated xylene isomer is subsequently circulated to the xylene separation unit process.

In such a xylene isomer separation and isomerization process, several on-line and off-line gas chromatography devices are typically used for analysis of process operations and process performances. In this case, about 10 minutes are taken to analyze a single component. A greatly increased amount of time is taken for the analysis of a multi-component material. For this reason, on-line gas chromatography devices have been used only to continuously check several essential components associated with an optimum process operation, thereby obtaining products with a good quality.

In order to achieve a more accurate control and an optimization for processes, it is essentially required to calculate process performances of all unit processes used and the entire process. For such a process performance calculation, it is also required to analyze all components of respective materials to be processed in unit processes and respective product streams emerging from those unit processes. Typically, such a component analysis is carried out by obtaining samples in the production field, and measuring required components from those samples in the laboratory using an off-line gas chromatography device. However, such procedures require a lot of time. For this reason, in the case of the above mentioned xylene isomer separation and isomerization process, the process performance analysis is carried out only one time in a week. Based on the analysis results, process parameters are controlled. The process performance of the xylene isomer separation and isomerization process varies frequently depending on various variations occurring at the upstream stage from each unit process where a raw material to be processed is supplied. However, conventional process performance monitoring and process parameter control, which are carried out based on a component analysis using on-line and off-line gas chromatography devices, can not effectively cope with such variations.

Information supplied from the monitoring system is used for an operation for each unit process. Also, operation parameters are controlled, based on analysis data about the raw material and the compositions at the columns used in the xylene separation unit process. In association with the para-xylene separation unit process, the process recovery rate can be monitored on the basis of analysis data about the raw material used in the para-xylene separation unit process and the material stream fed to the xylene isomerization unit process. It is also possible to determine the reactor temperature in the xylene isomerization unit process on the basis of analysis data about the raw material used in the xylene isomerization unit process and the final product stream.

Using information supplied from the monitoring system and by virtue of the provision of the process simulator, it is possible to determine an ethylbenzene conversion rate desired to obtain an optimum process yield. An increase in ethylbenzene conversion rate results in a reduction in the flow rate of a material stream circulating from the xylene isomerization unit process to the xylene separation unit process. In this case, however, an increase in the loss of xylene occurs. In this regard, there is an optimum ethylbenzene conversion.

As mentioned above, the near infrared analyzer system of the present invention analyzes respective compositions of material streams at five stages of the above mentioned process and sends the resultant analysis data to the monitoring system included in the process computer. Based on the results of the analysis as well as the compositions of material streams at five stages in the process, the near infrared analyzer system also calculates important process performance evaluation parameters for the xylene isomerization process, namely, ethylbenzene conversion, benzene selectivity, xylene loss, catalyst activity, para-xylene equilibrium constant, ortho-xylene equilibrium constant, para-xylene yield, and ortho-xylene yield. The calculated results are displayed through the monitoring system. The monitoring system also sends the calculated results to an operating unit in an on-line manner. Accordingly, it is possible to monitor the entire operation state of the process within 15 minutes in an on-line manner. Conventionally, 2 to 3 days are taken for the same monitoring. In the operating unit, process control parameters such as valve control parameters are controlled, based on data output from the monitoring system, in order to keep desired process conditions.

Meanwhile, the process simulator, which is commercially available, performs a process simulation for determining optimum process operation parameters, based on the measured results obtained from the near infrared analyzer system and the process performance evaluation parameters supplied from the monitoring system. The determined process operation parameters are sent to the operating unit.

The present invention will now be described in more detail in conjunction with an example provided for the present invention. However, the present invention should not be limited to this example.

EXAMPLE

In order to evaluate the prediction ability of the near infrared analyzer for a xylene isomer separation and isomerization process, 99 measured values obtained after an near infrared analysis carried out in an on-line manner for one month using the system of FIG. 2 were compared with those obtained using a conventional gas chromatography. The results are shown in the following Table 1.

In order to make calibration equations, samples extracted in the xylene isomer separation and isomerization process were used. By virtue of the development and prediction of such calibration equations, it was possible to obtain a superior correlation between the near infrared analysis and the conventional gas chromatography analysis.

Based on the results shown in Table 1, the process yield of the entire process was calculated. Also, calculation was made for important process performance evaluation parameters for the xylene isomerization process, namely, ethylbenzene conversion, benzene selectivity, xylene loss, catalyst activity, para-xylene equilibrium constant, ortho-xylene equilibrium constant, para-xylene yield, and ortho-xylene yield. The calculated results are displayed through the monitoring system.

The para-xylene yield $Y_{PX}$ in the entire process is expressed by the following Equation 1:

$$Y_{PX} = 100 \times \frac{F_{PX}}{C_{X,F} \times F_F} \quad \text{[Equation 1]}$$

where, $F_{PX}$ represents the flow rate of a para-xylene product, $F_F$ represents the flow rate of a para-xylene raw material, and $C_{X,F}$ represents the xylene content of the para-xylene raw material.

Also, the ortho-xylene yield $Y_{OX}$ in the entire process is expressed by the following Equation 2:

$$Y_{OX} = 100 \times \frac{F_{OX}}{C_{X,F} \times F_F} \quad \text{[Equation 2]}$$

where, $F_{OX}$ represents the flow rate of an ortho-xylene product.

The loss of xylene, $L_{OX}$, in the entire process is expressed by the following Equation 3:

$$L_{OX} = 100 \times \left[1 - \frac{C_{PX,PX} \times F_{PX} + C_{OX,OX} \times F_{OX}}{C_{X,F} \times F_F}\right] \quad \text{[Equation 3]}$$

where, $C_{PX,PX}$ represents the para-xylene content of the para-xylene product, and $C_{OX,OX}$ represents the ortho-xylene content of the ortho-xylene product.

The ethylbenzene conversion rate $E_{EB}$ in the xylene isomerization unit process is expressed by the following Equation 4:

$$\xi_{EB} = 100 \times \left[1 - \frac{C_{EB,DO} \times F_{DO} + C_{EB,DB} \times F_{DB}}{C_{EB,IF} \times F_{IF}}\right] \quad \text{[Equation 4]}$$

where, $C_{EB,DO}$ represents the ethylbenzene content at the top of a deheptanizer column, $C_{EB,DB}$ represents the ethylbenzene content at the bottom of the deheptanizer column, $C_{EB,IF}$ represents the ethylbenzene content of a raw material used in the xylene isomerization unit process, $F_{DO}$ represents the flow rate at the top of the deheptanizer column, $F_{DB}$ represents the flow rate at the bottom of the deheptanizer column, and $F_{IF}$ represents the flow rate of the raw material used in the xylene isomerization unit process.

Also, the para-xylene conversion rate $E_{PX}$ in the xylene isomerization unit process is expressed by the following Equation 5:

$$\xi_{PX} = 100 \times \frac{C_{PX,DO} \times F_{DO} + C_{PX,DB} \times F_{DB}}{C_{X,DO} \times F_{DO} + C_{X,DB} \times F_{DB}} \quad \text{[Equation 5]}$$

where, $C_{PX,DO}$ represents the para-xylene content at the top of the deheptanizer column, $C_{PX,DB}$ represents the para-xylene content at the bottom of the deheptanizer column, $C_{X,DO}$ represents the xylene content at the top of the deheptanizer column, and $C_{X,DB}$ represents the xylene content at the bottom of the deheptanizer column.

The ortho-xylene conversion rate $E_{OX}$ in the xylene isomerization unit process is expressed by the following Equation 6:

$$\xi_{OX} = 100 \times \frac{C_{OX,DO} \times F_{DO} + C_{OX,DB} \times F_{DB}}{C_{X,DO} \times F_{DO} + C_{X,DB} \times F_{DB}} \quad [\text{Equation 6}]$$

where, $C_{OX,DO}$ represents the ortho-xylene content at the top of the deheptanizer column, and $C_{OX,DB}$ represents the ortho-xylene content at the bottom of the deheptanizer column.

The para-xylene equilibrium constant $\Pi_{PX}$ in the xylene isomerization unit process is expressed by the following Equation 7:

$$\Gamma_{PX} = \frac{P_{PX} + \xi_{PX}}{P_{PX} + X_{PX,IF}} \quad [\text{Equation 7}]$$

where, $P_{PX}$ represents the equilibrium concentration of para-xylene, and $X_{PX,IF}$ represents the para-xylene content of the entire xylene in the raw material used in the xylene isomerization unit process.

The ortho-xylene equilibrium constant $\Gamma_{OX}$ in the xylene isomerization unit process is expressed by the following Equation 8:

$$\Gamma_{OX} = \frac{P_{OX} + \xi_{OX}}{P_{OX} + X_{OX,IF}} \quad [\text{Equation 8}]$$

where, $P_{OX}$ represents the equilibrium concentration of ortho-xylene, and $X_{OX,IF}$ represents the ortho-xylene content of the entire xylene in the raw material used in the xylene isomerization unit process.

The catalyst activity A in the xylene isomerization unit process is expressed by the following Equation 9:

$$A = -(LHSV) \times \ln\left[1 - \frac{\xi_{EB}}{100}\right] \times e^{\left[\frac{\Delta E}{R}\left(\frac{1}{T} - \frac{1}{T_0}\right)\right]} \quad [\text{Equation 9}]$$

where, LHSV represents the space velocity of a liquid per time, $\Delta E$ represents activation energy for a dialkylation, R represents the ideal gas constant, T represents a reactor temperature, and To represents a reference reactor temperature.

Also, the benzene selectivity $S_{RZ}$ in the xylene isomerization unit process is expressed by the following Equation 10:

$$S_{BZ} = 100 \times \frac{M_{BZ,DO} + M_{BZ,DB} + M_{BZ,DG} - M_{BZ,IF}}{M_{EB,IF} + M_{EB,DO} - M_{EB,DB} - M_{EB,DG}} \quad [\text{Equation 10}]$$

where, $M_{BZ,DO}$ represents the benzene mole % at the top of the diheptanizer column, $M_{BZ,DB}$ represents the benzene mole % at the bottom of the diheptanizer column, $M_{BZ,DG}$ represents the benzene mole % in an off gas from the diheptanizer column, $M_{BZ,IF}$ represents the benzene mole % in the raw material used in the xylene isomerization unit process, $M_{EB,DO}$ represents the ethylbenzene mole % at the top of the diheptanizer column, $M_{EB,DB}$ represents the ethylbenzene mole % at the bottom of the diheptanizer column, $M_{EB,DG}$ represents the ethylbenzene mole % in an off gas from the diheptanizer column, and $M_{EB,IF}$ represents the ethylbenzene mole % in the raw material used in the xylene isomerization unit process.

Finally, the xylene loss rate $L_X$ in the xylene isomerization unit process is expressed by the following Equation 11:

$$L_X = 100 \times \left[1 - \frac{C_{X,DO} \times F_{DO} + C_{X,DB} \times F_{DB}}{C_{X,IF} \times F_{IF}}\right] \quad [\text{Equation 11}]$$

where, $C_{X,DO}$ represents the xylene content at the top of the diheptanizer column, $C_{X,DB}$ represents the xylene content at the bottom of the diheptanizer column, and $C_{X,IF}$ represents the xylene content in the raw material used in the xylene isomerization unit process.

The information supplied from the monitoring system is used for operations of unit processes, namely, the xylene separation unit process, para-xylene separation unit process, and xylene isomerization unit process. Operation parameters are controlled on the basis of analysis data about the composition of the raw material used in the xylene separation unit process and the composition at the top of each column used in the xylene separation unit process. When the non-aromatic component contained in the raw material processed in the xylene separation unit process is more than that for a normal process operation, the separation degree of the process decreases. In order to improve the separation degree, the heat quantity and reflux quantity of a reboiler included in the distillation column increases. When the ortho-xylene component contained in the raw material processed in the xylene separation unit process is more than that for a normal process operation in the production of ortho-xylene, the para-xylene content at the top of the column is less than that for the normal process operation. In order to control the para-xylene content, the flow rate of the raw material and the flow rate at the bottom of the column increase. For the operation of the para-xylene separation unit process, the control parameters of the absorption column are then controlled, using information about the composition of the raw material used in the para-xylene isomerization unit process, in order to achieve an increase in the recovery rate of para-xylene while maintaining a desired purity of the product. Finally, for the xylene isomerization unit process, the reactor temperature in the xylene isomerization unit process is controlled so that the ethylbenzene conversion rate calculated in the monitoring system corresponds to a set value. The set value for the ethylbenzene conversion rate is determined in the process of an optimization for the entire process which will be described, hereinafter. An increase in the reactor temperature results in an increase in the ethylbenzene conversion rate. In order to maintain the ethylbenzene conversion rate to correspond to the set value, the reactor temperature is appropriately determined by use of a feedback control or a feedforward control using a process model.

The information supplied from the monitoring system is also used for an optimization for the entire process. In order to optimize the productivity of the entire process, an appropriate set value for the ethylbenzene conversion rate in the xylene isomerization unit process should be determined after an optimization for control parameters of each unit process. An increase in the ethylbenzene conversion rate results in a reduction in the flow rate of a material circulating from the xylene isomerization unit process to the xylene separation unit process. In this case, accordingly, it is possible to process an increased amount of raw materials, thereby achieving an improvement in productivity. However, a xylene destruction reaction, which is a side reaction of the ethylbenzene conversion, increases. As a result, an increase in xylene loss occurs. In order to derive an optimum ethylbenzene conversion rate, therefore, an optimization problem for maximizing the following target function should be solved by controlling the ethylbenzene conversion rate.

Target Function:

$$P_{PX} \times F_{PX} + P_{OX} \times O_{OX} \times F_{OX} + I_{DZ} \times P_{DZ} - P_X \times F_X - P_U \times F_U$$

Limitative Conditions:

$$F_{FX}, F_{OX}, F_{BZ}, F_X, F_U, \xi_{EB}$$

Control Parameter: $\xi_{EB}$ where, $P_{PX}$, $P_{OX}$, $P_{BZ}$, $P_X$ and $P_U$ represent the prices of para-xylene, ortho-xylene, benzene, xylene, and utilities, respectively, $F_{PX}$, $F_{OX}$, and $F_{BZ}$, represent the productivities of para-xylene, ortho-xylene, and benzene, respectively, $F_X$, and $F_U$, represent the consumed amounts of xylene and utilities, respectively, and $$\xi_{EB}$$

represents a maximum ethylbenzene conversion rate. The reactor temperature of the xylene isomerization unit process has a maximum value due to limitations involved in the equipment. For this reason, the ethylbenzene conversion rate also exhibits a maximum value. It can be assumed that the same products have a constant price determined by a given market situation. Meanwhile, it is possible to simulate process characteristics for determining the production and consumption amounts of products, by use of a general process simulator. Where the process simulator is tuned using previous operation conditions of the process, it is possible to estimate variations in the production and consumption amounts of products depending on a variation in ethylbenzene conversion rate, during the period in which the optimization problem is solved. The optimum ethylbenzene conversion rate derived by the solution of the optimization problem varies continuously depending on a variation in the price of products and variations in the equipment for the process.

Estimated errors shown in the following Table 1 are absolute errors of measured values, obtained by the near infrared measurement method, compared to those obtained by the gas chromatography measurement method. These estimated errors are indicia representing the accuracy of the near infrared measurement method. In Table 1, correlation coefficients are indicia representing the correlation between the near infrared measurement method and the gas chromatography method. The repeatability of the near infrared measurement method shown in Table 1 represents a standard deviation of measured values obtained by the near infrared measurement method where the same samples are continuously measured.

TABLE 1

| | Measurement Items | Measurement Range | Estimation Error | Correlation Coeffcient | Repeatability |
|---|---|---|---|---|---|
| MP* | Ortho-Xylene | 15~28% | 0.33% | 0.9996 | ±0.043% |
| | Meta-Xylene | 38~65% | 0.38% | 0.9997 | ±0.055% |

TABLE 1-continued

| | Measurement Items | Measurement Range | Estimation Error | Correlation Coeffcient | Repeatability |
|---|---|---|---|---|---|
| | Para-Xylene | 3~24% | 0.15% | 0.9998 | ±0.032% |
| | Ethylbenzene | 3~17% | 0.13% | 0.9997 | ±0.031% |
| | Toluene | 0.0~0.7% | 0.08% | 0.9624 | ±0.001% |
| | Non-Aromatic Hydrocarbon | 0.2~0.8% | 0.05% | 0.9885 | ±0.008% |
| | Arometic Hydrocarbon of C9 or More | 0.0~1.2% | 0.08% | 0.9906 | ±0.046% |
| MP** | Benzene | 71~79% | 0.58% | 0.9709 | — |
| | Toluene | 19~26% | 0.50% | 0.9717 | — |
| | Non-Arometic Hydrocarbon | 1.7~4.8% | 0.25% | 0.9630 | — |
| | Xylene Isomer | 0.0~0.9% | 0.08% | 0.9918 | — |

MP* (Measurement Point*): Xylene Feed Stage, Upstream Stage from Para-Xylene Separation Unit Process, Upstream Stage from Xylene Isomerization Process, and Lower-Side Downstream Stage from C7 Separation Process
MP (Measurement Point): Upper-Side Downstream Stage from C7 Separation Process As apparent from Table 1, the near infrared measurement method exhibited an accuracy capable of a replacement of the gas chromatography therewith for the measurement for the contents of ortho-xylene, meta-xylene, para-xylene, ethylbenzene, non-aromatic hydrocarbon, toluene, benzene, and aromatic hydrocarbon having nine carbon atoms or more. The repeatability of the near infrared measurement method was superior to that of the gas chromatography.

As apparent from the above description, the near infrared analyzer system according to the present invention calculates process performance evaluation parameters based on the compositions of material streams at five stages in a xylene isomer separation and isomerization process as well as the results of an analysis performed. The process performance evaluation parameters include ethylbenzene conversion, benzene selectivity, xylene loss, catalyst activity, para-xylene equilibrium constant, ortho-xylene equilibrium constant, para-xylene yield, and ortho-xylene yield. The calculated results are supplied to an operating unit via a monitoring system in an on-line manner within 15 minutes. Accordingly, it is possible to monitor the entire operation state of the process within 15 minutes in an on-line manner. Conventionally, 2 to 3 days are taken for the same monitoring. In the operating unit, process control parameters such as valve control parameters are controlled, based on data output from the monitoring system, in order to keep desired process conditions.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A method for controlling and optimizing a xylene isomer separation and isomerization process using a near infrared analyzer system, comprising the steps of:

(A) extracting samples at the upstream stage from a xylene separation unit process, the upstream stage from a para-xylene separation unit process, the upstream stage from a xylene isomerization process, the upper-side downstream stage of a C7 separation process, and the lower-side downstream stage of the C7 separation process, respectively;

(B) collecting the extracted samples in a fast loop via feed lines, respectively;

(C) carrying out a primary heat exchange in a primary heat exchange system for the samples fed from the fast loop by cooling water supplied from a cooling water line;

(D) determining whether or not respective temperatures of the samples heat-exchanged in the primary heat exchange system are not more than a first predetermined temperature;

(E) secondarily cooling the samples, which have been cooled to the first predetermined temperature or less, by a chiller included in a secondary cooling system;

(F) determining whether or not respective temperatures of the samples cooled in the secondary cooling system are not more than a second predetermined temperature;

(G) sequentially selecting the samples cooled to the second predetermined temperature or less by a stream selector, and determining which sample has been selected from the first to the fifth samples;

(H) partially extracting the sequentially selected samples by desired amounts, respectively, while returning the remaining portions of the samples to step (A) via first return lines, the fast loop, and second return lines;

(I) sequentially detecting the components of the samples each extracted by a desired amount, by use of a probe, and then sequentially returning the samples to a sample recovery line via a third feed return line;

(J) sequentially analyzing the samples, detected by the probe, in a near infrared analyzer, in accordance with a near infrared spectroscopy, in terms of ethylbenzene conversion, benzene selectivity, xylene loss, catalyst activity, para-xylene equilibrium constant, ortho-xylene equilibrium constant, para-xylene yield, and ortho-xylene yield;

(K) sending data, obtained after the analysis for the samples in the near infrared analyzer, to a distributed control system in an on-line manner;

(L) sending data resulting from a processing for the analysis data in the distributed control system to a process computer;

(M) outputting the data received in the process computer in the form of a signal easily recognizable by an operator;

(N) recognizing the data, which is displayed by the process computer, by the operator, inputting a desired command value by the operator, based on his determination made after his recognition, to the distributed control system; and (O) determining the input command value, thereby controlling valves for the samples to be opened or closed.

2. An apparatus for controlling and optimizing a xylene isomer separation and isomerization process using a near infrared analyzer system, comprising:

feed lines for extracting samples at a xylene feed stage, the upstream stage from a para-xylene separation unit process, the upstream stage from a xylene isomerization process, the upper-side downstream stage from a C7 separation process, and the lower-side downstream stage from the C7 separation process;

a fast loop for accelerating the samples fed thereto via the feed lines to a predetermined flow rate or more;

a primary heat exchange system for performing heat exchange with the samples fed thereto in an accelerated state, thereby cooling the samples to a first predetermined temperature;

a secondary cooling system for secondarily cooling the samples, primarily cooled in the primary heat exchange system, to a second predetermined temperature;

a cooling water line for supplying cooling water to the primary heat exchange system;

a chiller for cooling the cooling water introduced from the cooling water line to a desired temperature and then supplying the cooled water to the secondary cooling system;

a stream selector for sequentially selecting and discharging the samples cooled to a desired temperature in the secondary cooling system;

a probe for detecting the components of a sample selectively fed thereto in a desired quantity;

first return lines for returning the remaining portions of the samples, except for the sample portions fed to the probe for the component detection, to the fast loop, in an accelerated state;

second return lines for returning the samples, returned via the first return lines and accelerated again by the fast loop, to the upstream stage from the xylene separation unit process, the upstream stage from the para-xylene separation unit process, the upstream stage from the xylene isomerization process, the upper-side downstream stage of the C7 separation process, and the lower-side downstream stage of the C7 separation process, respectively;

a third return line for returning the sample from the probe to a sample recovery line after the component detection for the sample by the probe is completed;

a near infrared analyzer for analyzing component data detected by the probe and outputting the analyzed result in the form of an electrical signal in an on-line manner;

a distributed control system for performing a distributed control for data received from the near infrared analyzer, sending the resultant signal to a process computer, determining a command value inputted by an operator on the basis of the result of his comparison for the data displayed through the process computer with set data, and performing a control for opening and closing a valve associated with the data; and the process computer for displaying the data received from the distributed control system in such a fashion that the operator can easily recognize the displayed data, and outputting the data.

3. The apparatus according to claim 2, wherein the first return lines, the second return lines, and the third return line are configured to automatically recover the samples by virtue of a pressure difference between the stream selector and the fast loop, a pressure difference between the fast loop and each of the unit processes, and a pressure difference between the probe and the sample recovery line.

4. The apparatus according to claim 2, wherein the process computer comprises:

a monitoring system provided with display means for displaying data in such a fashion that the operator can easily recognize the displayed data with the naked eye; and a process simulator for carrying out a process simulation for determining optimum process operation parameters, based on the measured results obtained from the near infrared analyzer and the process performance evaluation parameters supplied from the monitoring system, the process simulator also having a function for copying or transmitting the data displayed on the monitoring system.

5. The apparatus according to claim 2, wherein the first predetermined temperature is not more than 45° C.

6. The apparatus according to claim 2, wherein the second predetermined temperature is not more than 25° C.

7. The apparatus according to claim 2, wherein the stream selector is provided with a plurality of electronic valves adapted to sequentially send respective portions of the samples introduced therein to the probe while also sending the remaining portions of the samples to first return lines, respectively.

8. The apparatus according to claim 2, further comprising means for automatically opening and closing the valve, based on data set in the distributed control system without controlling the valve by a manual operation of the operator based on his determination on the basis of the data displayed through the process computer.

9. The apparatus according to claim 2, wherein the feed lines and the first return lines, the second return lines, and the third return line have a minimum diameter in so far as they can feed a liquid therethrough.

* * * * *